United States Patent
Chen

(10) Patent No.: US 11,378,504 B2
(45) Date of Patent: Jul. 5, 2022

(54) RUBBER DETECTION SYSTEM

(71) Applicant: KAUO JEI IND CO., LTD., New Taipei (TW)

(72) Inventor: Wen-Ho Chen, New Taipei (TW)

(73) Assignee: KAUO JEI IND CO., LTD., New Taipei (TW)

( * ) Notice: Subject to any disclaimer, the term of this patent is extended or adjusted under 35 U.S.C. 154(b) by 404 days.

(21) Appl. No.: 16/568,232

(22) Filed: Sep. 11, 2019

(65) Prior Publication Data

US 2021/0072130 A1    Mar. 11, 2021

(51) Int. Cl.
| | |
|---|---|
| *G01N 11/00* | (2006.01) |
| *G01N 33/44* | (2006.01) |
| *G01N 9/00* | (2006.01) |
| *G01N 3/20* | (2006.01) |
| *G01N 3/18* | (2006.01) |

(52) U.S. Cl.
CPC .............. *G01N 11/00* (2013.01); *G01N 3/18* (2013.01); *G01N 3/20* (2013.01); *G01N 9/00* (2013.01); *G01N 33/445* (2013.01)

(58) Field of Classification Search
CPC . G01N 11/00; G01N 3/18; G01N 3/20; G01N 9/00; G01N 33/445
See application file for complete search history.

(56) References Cited

FOREIGN PATENT DOCUMENTS

| CN | 106802263 A | * | 6/2017 | |
|---|---|---|---|---|
| CN | 106802263 A | | 6/2017 | |
| JP | 04249756 A | * | 12/1990 | |
| JP | 04249756 A | * | 9/1992 | |
| JP | H04249756 A | | 9/1992 | |
| JP | 2006116835 A | * | 5/2006 | |
| JP | 2008223780 A | * | 9/2008 | ........... F16J 15/3284 |
| JP | 2011214978 A | * | 10/2011 | |
| JP | 2011214978 A | | 10/2011 | |
| TW | 200844410 A | | 11/2008 | |

* cited by examiner

*Primary Examiner* — Herbert K Roberts
*Assistant Examiner* — Fatemeh Esfandiari Nia
(74) *Attorney, Agent, or Firm* — Chun-Ming Shih; HDLS IPR Services

(57) ABSTRACT

A rubber detection system for rubber raw material includes a controller, a rubber sampling module, a rubber calender, a temperature control module, a mooney sensor, a power meter, an expansion ratio detection module, a rotation counter, and a specific gravity detection module. The rubber sampling module obtains a rubber to be tested consistent with a weight value. After the temperature control module determines that the rubber to be tested has reached a temperature value, the rubber calender outputs the rubber to be tested having a thickness value. The power meter records and obtains a power consumption value form the rubber calender. The expansion ratio detection module obtains an expansion ratio based on the thickness value and a roller spacing. The rotation counter obtains the number of rotations of the rubber calender. The specific gravity detection module obtains an actual specific gravity value of the rubber to be tested.

16 Claims, 7 Drawing Sheets

RUBBER DETECTION SYSTEM

BACKGROUND

Technical Field

The present disclosure relates to a rubber detection system, and more particularly to a rubber detection system for rubber processing.

Description of Related Art

The statements in this section merely provide background information related to the present disclosure and do not necessarily constitute prior art.

In the field of rubber testing, such as the national standard of the People's Republic of China (GB), the International Organization for Standardization (ISO), the American Society for Testing and Materials (ASTM), and Rubber Research Institute of Malaysia (RRIM), outside of North America, ISO standards have gradually become popular.

However, in the field of rubber testing, there is still a lack of a one-stop system for rapid and continuous detection of rubber. Moreover, when rubber is actually produced and applied to a commercial production line, since a sampling weight value of rubber, a roller pitch of a rubber calender and a temperature of a rubber to be tested cannot be accurately controlled according to the rubber to be tested having a specific sampling weight, and then, an accurate expansion ratio, a power consumption value, a mechanical loss value and an actual specific gravity value cannot be obtained. This has caused problems for rubber testing companies and rubber-related manufacturers, and increased production costs.

Therefore, how to design a rubber detection system to solve the technical problems above is an important subject studied by the inventors and proposed in the present disclosure.

SUMMARY

The purpose of the present disclosure is to provide a rubber detection system, which can accurately control a sampling weight value of rubber, a roller pitch of a rubber calender and a temperature of a rubber to be tested according to the rubber to be tested having a specific sampling weight, thereby obtaining an accurate expansion ratio, a power consumption value, a mechanical loss value and an actual specific gravity value. And to achieve the purpose of reducing the production costs of rubber-related manufacturing.

In order to achieve the purpose above-mentioned, the rubber detection system for rubber raw material includes a controller, a rubber sampling module, a rubber calender, a temperature control module, a mooney sensor, a power meter, an expansion ratio detection module, a rotation counter, and a specific gravity. The controller produces a first weight value, a second weight value, a third weight value, a first temperature value, a target mooney index, a first roller pitch and a second roller pitch G. The rubber sampling module coupled to the controller, and the rubber sampling module samples the rubber raw material according to the first weight value to obtain a first rubber to be tested consistent with the first weight value, and the rubber sampling module samples the first rubber to be tested according to the second weight value to obtain a second rubber to be tested consistent with the second weight value, and the rubber sampling module samples the rubber raw material according to the third weight value to obtain a third rubber to be tested consistent with the third weight value. The rubber calender coupled to the controller and the rubber sampling module, the rubber calender including two rollers arranged in parallel, the two rollers spaced apart from each other by the first roller pitch and continuously calendering the first rubber to be tested at least six times, and the two rollers spaced apart from each other by the second roller pitch G and continuously calendering the second rubber to be tested two times. The temperature control module coupled to the controller and the rubber calender, the temperature control module maintaining the first rubber to be tested or the second rubber to be tested to have the first temperature value, when the temperature control module determining that the first rubber to be tested in the rubber calender has reached the first temperature value, the two rollers continuously calender the first rubber to be tested at least six times, and when the temperature control module determining that the second rubber to be tested in the rubber calender has reached the first temperature value, the two rollers continuously calender the second rubber to be tested two times, and the rubber calender outputs the second rubber to be tested having a thickness value D. The mooney sensor coupled to the controller, the temperature control module, and the rubber calender, when the temperature control module determining that the first rubber to be tested in the rubber calender has reached the first temperature value, the mooney sensor obtains an actual mooney index from the first rubber to be tested in the rubber calender, and the controller controls the two rollers has the number of calendering the first rubber to be tested according to the target mooney index and the actual mooney index, until the target mooney index being consistent with the actual mooney index. The power meter coupled to the controller, the mooney sensor, and the rubber calender, when the mooney sensor determining that the target mooney index consistent with the actual mooney index, the power meter records and obtains a power consumption value form the rubber calender. The expansion ratio detection module coupled to the controller and the rubber calender, the expansion ratio detection module obtains an expansion ratio $E=2D/G$ according to twice the thickness value D and the second roller pitch G. The rotation counter coupled to the controller, the temperature control module, the mooney sensor, and the rubber calender, when the temperature control module determining that the first rubber to be tested in the rubber calender has reached the first temperature value, the rotation counter counts number of rotating 360 degrees of the two rollers until the target mooney index being consistent with the actual mooney index, and the rotation counter obtains a mechanical loss value. The specific gravity detection module coupled to the controller and the rubber sampling module, the specific gravity detection module applies a pressure of 2.3 metric tons to the third rubber to be tested, and then, the specific gravity detection module obtains an actual specific gravity value S by detection a volume of the third rubber to be tested. The second roller pitch G is changed in a minimum unit of 0.001 mm depending on the number of calendaring the first rubber to be tested, and the second roller pitch G is between 0.065 mm and 0.145 mm.

In one embodiment, the first weight value is 360 grams, the second weight value is 25 grams, and the third weight value is 1 kilogram.

In one embodiment, the first temperature value is 25 degrees Celsius.

In one embodiment, the target mooney index has a mooney viscosity between 61.07 and 91.06.

In one embodiment, the first roller pitch is 1.65 mm, and the second roller pitch G is 0.065 mm.

In one embodiment, the two rollers include a front roller and a rear roller, when the two rollers continuously calendering the first rubber to be tested, the front roller rotates between 21 rpm and 24 rpm, and the rear roller rotates at 31 rpm, and when the two rollers continuously calendering the second rubber to be tested, a speed ratio of the two rollers is 1:1.

In one embodiment, when the two rollers continuously calendering the first rubber to be tested, the speed ratio of the two rollers is 1:1.4.

In one embodiment, the power meter obtains the power consumption value by subtracting a power of the previous record from a power of the current record of the rubber calender.

In one embodiment, the temperature control module is a water-cooled chiller.

In one embodiment, the rubber detection system further includes a plasticity detection module, the plasticity detection module folds the second rubber to be tested that has been continuously calendered two times, and the plasticity detection module cuts out a cylinder having a thickness with twice the thickness value D, and then, the plasticity detection module heats the cylinder to a second temperature value, and applies a pressure with 10 kg to the cylinder and release the cylinder after maintaining the pressure with 10 kg for 15 seconds, the plasticity detection module obtains a first rebound thickness of the cylinder after first impact and rebound moment for the cylinder, and the plasticity detection module outputs an initial plasticity value, the first rebound thickness has a minimum unit of 0.01 mm.

In one embodiment, the second temperature value is 100 degrees Celsius.

In one embodiment, the rubber detection system further includes a plasticity detection module, the plasticity detection module folds the second rubber to be tested that has been continuously calendered two times, and cuts out a cylinder having a thickness with twice the thickness value D, and then, the cylinder being heated to 140 degrees Celsius and being cooled after the cylinder being maintained 140 degrees Celsius for 30 minutes, finally, the plasticity detection module heats the cylinder to a second temperature value, and the plasticity detection module applies a pressure with 10 kg to the cylinder and release the cylinder after maintaining the pressure with 10 kg for 15 seconds, the plasticity detection module obtains a first rebound thickness of the cylinder after first impact and rebound moment for the cylinder, and the plasticity detection module outputs an initial plasticity value, the first rebound thickness has a minimum unit of 0.01 mm.

In one embodiment, the rubber detection system further includes an identification module, the identification module is coupled to the controller, and the identification module controls an access authority of the power consumption value, the expansion ratio E, the mechanical loss value, the actual specific gravity value S and the doping ratio X by combination with at least one of NFC, RFID, fingerprint, voiceprint, face recognition, retina, and password.

In one embodiment, the rubber detection system further includes a doping identification module coupled to the controller and the specific gravity detection module, and the doping identification module obtains a doping ratio X of a skim rubber in the rubber raw material according to the actual specific gravity value S and a target specific gravity value T, the skim rubber has a specific gravity value K and satisfies the following relationship: $X=(S-T)/(K-T)\times 100$.

In one embodiment, the target specific gravity value T is 0.9149, and the specific gravity value K of the skim rubber is 0.9783.

In one embodiment, the rubber detection system further includes a cloud server, the cloud server stores the power consumption value, the expansion ratio E, the mechanical loss value, the actual specific gravity value S, and the doping ratio X.

When operating the expansion ratio detection system, the controller causes the rubber sampling module to obtain the first rubber to be tested, the second rubber to be tested or the third rubber to be tested according to the first weight value, the second weight value or the third weight value.

Afterward, the temperature control module maintaining the first rubber to be tested or the second rubber to be tested to have the first temperature value. When the temperature control module determines that the first rubber to be tested in the rubber calender has reached the first temperature value, the two rollers spaced apart from each other by the first roller pitch and continuously calendering the first rubber to be tested at least six times. When the temperature control module determines that the second rubber to be tested in the rubber calender has reached the first temperature value, the two rollers spaced apart from each other by the second roller pitch G and continuously calendering the second rubber to be tested two times, and the rubber calender outputs the second rubber to be tested having a thickness value D.

Finally, the expansion ratio detection module obtains the expansion ratio $E=2D/G$ according to twice the thickness value D and the second roller pitch G. The rotation counter and the power meter respectively obtain the mechanical loss value and the power consumption value through the actual mooney index obtained by the mooney sensor and the target mooney index generated by the controller. The specific gravity detection module may obtain the actual specific gravity value S by sorting or synchronizing with the foregoing steps.

To this end, according to the rubber has a specific number of calendering the rubber and the rubber to be tested has the weight value as a specific sampling weight, the present disclosure can accurately control the second roller pitch G of the rubber calender (the second roller pitch G is changed in a minimum unit of 0.001 mm depending on the number of calendering the rubber) and the temperature value of the rubber to be tested (as the first temperature value or the second temperature value). Thereby obtaining an accurate the expansion ratio E, the power consumption value, the mechanical loss value, and the actual specific gravity value S, and achieving the purpose to reduce the production cost of the rubber-related manufacturing industry.

In order to further understand the techniques, means, and effects of the present disclosure for achieving the intended purpose. Please refer to the following detailed description and drawings of the present disclosure. The drawings are provided for reference and description only, and are not intended to limit the present disclosure.

DETAILED DESCRIPTION

Figure 1:
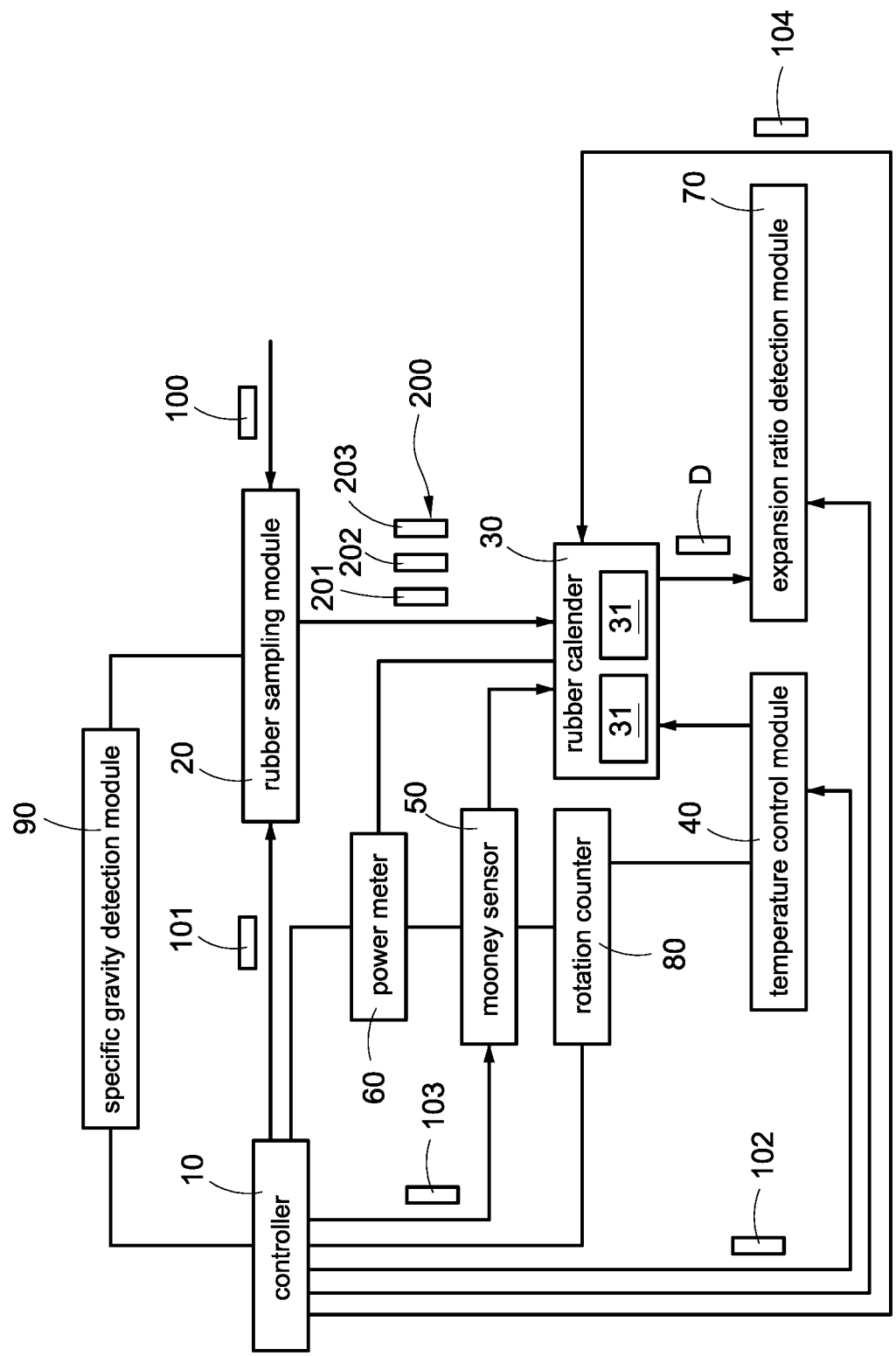
FIG. 1 is an architectural diagram of a first embodiment of a rubber detection system of the present disclosure.

The embodiments of the present disclosure are described by way of specific examples, and those skilled in the art can readily appreciate the other advantages and functions of the present disclosure. The present disclosure may be embodied or applied in various other specific embodiments, and various modifications and changes can be made without departing from the spirit and scope of the present disclosure.

It should be understood that the structures, the proportions, the sizes, the number of components, and the like in the drawings are only used to cope with the contents disclosed in the specification for understanding and reading by those skilled in the art, and it is not intended to limit the conditions that can be implemented in the present disclosure, and thus is not technically significant. Any modification of the structure, the change of the proportional relationship, or the adjustment of the size, should be within the scope of the technical contents disclosed by the present disclosure without affecting the effects and the achievable effects of the present disclosure.

The technical content and detailed description of the present disclosure will be described below in conjunction with the drawings.

Please refer to FIG. 1, which shows an architectural diagram of a first embodiment of a rubber detection system of the present disclosure.

The rubber detection system of the present disclosure is applied to a rubber raw material 100, including a controller 10, a rubber sampling module 20, a rubber calender 30, a temperature control module 40, a mooney sensor 50, a power meter 60, an expansion ratio detection module 70, a rotation counter 80, and a specific gravity detection module 90. The controller 10 produces a weight value 101, a first temperature value 102, a target mooney index 103, and a roller pitch 104. The controller 10 may be one of a CPU, an MPU, an ASIC, and a SoC. The weight value 101 includes a first weight value, a second weight value, and a third weight value. The roller pitch 104 includes a first roller pitch and a second roller pitch G. In the first embodiment of the present disclosure, the rubber raw material 100 may be Standard Indonesia Rubber No. 20 (SIR20).

The rubber sampling module 20 is coupled to the controller 10, and the rubber sampling module 20 samples the rubber raw material 100 according to the weight value 101 to obtain a rubber to be tested 200 consistent with the weight value 101. The rubber to be tested 200 includes a first rubber to be tested 201, a second rubber to be tested 202, and third rubber to be tested 203. The rubber sampling module 20 may be a device consisting of a robot arm, a cutter, and a conveyor belt. In the first embodiment of the present disclosure, the rubber sampling module 20 samples the rubber raw material 100 according to the first weight value to obtain a first rubber to be tested 201 consistent with the first weight value, and the rubber sampling module 20 samples the rubber raw material 100 according to the second weight value to obtain a second rubber to be tested 202 consistent with the second weight value, and the rubber sampling module 20 samples the rubber raw material 100 according to the third weight value to obtain a third rubber to be tested 203 consistent with the third weight value. The first weight value is 360 grams, the second weight value is 25 grams, and the third weight value is 1 kilogram.

The rubber calender 30 is coupled to the controller 10 and the rubber sampling module 20. The rubber calender 30 includes two rollers 31 arranged in parallel, and the two rollers 31 are spaced apart from each other by the roller pitch 104. The two rollers 31 are spaced apart from each other by the first roller pitch and continuously calenders the first rubber to be tested 201 at least six times. The two rollers 31 are spaced apart from each other by the second roller pitch G and continuously calenders the second rubber to be tested 202 two times. The first roller pitch is 1.65 mm. The second roller pitch G is changed in a minimum unit of 0.001 mm depending on the number of calendering the rubber (the number of calendering the rubber is at least six times), and the second roller pitch G is between 0.065 mm and 0.145 mm. The two rollers 31 include a front roller and a rear roller.

In the first embodiment of the present disclosure, the number of calendering the rubber is six times, the front roller rotates between 21 rpm and 24 rpm, and the rear roller rotates at 31 rpm, the optimum speed ratio of the front roller to the rear roller is 1:1.4. When the two rollers 31 calender the second rubber to be tested 202, the second roller pitch G is 0.065 mm, and an optimum speed ratio of the two rollers 31 is 1:1.

The temperature control module 40 is coupled to the controller 10 and the rubber calender 30, and the temperature control module 40 maintains the first rubber to be tested 201 or the second rubber to be tested 202 to have the first temperature value 102. When the temperature control module 40 determines that the first rubber to be tested 201 in the rubber calender has reached the first temperature value 102, the two rollers 31 continuously calender the first rubber to be tested 201 at least six times. When the temperature control module 40 determines that the second rubber to be tested 202 in the rubber calender has reached the first temperature value 102, the two rollers 31 continuously calender the second rubber to be tested 202 two times, and the rubber calender 30 outputs the second rubber to be tested 202 having a thickness value D. In a first embodiment of the present disclosure, the first temperature value 102 is 25 degrees Celsius. In the first embodiment of the present disclosure, the temperature control module 40 is a water-cooled chiller.

The mooney sensor 50 is coupled to the controller 10, the temperature control module 40, and the rubber calender 30. When the temperature control module 40 determines that the first rubber to be tested 201 in the rubber calender 30 has reached the first temperature value 102, the mooney sensor 50 obtains an actual mooney index (not shown) from the first rubber to be tested 201 in the rubber calender 30. The controller 10 controls the two rollers 31 having the number of calendering the first rubber to be tested 201 according to the target mooney index 103 and the actual mooney index, until the target mooney index 103 is consistent with the actual mooney index. In the first embodiment of the present disclosure, the target mooney index 103 has a mooney viscosity between 61.07 and 91.06. The mooney viscosity is a comprehensive index of hardness, viscosity, and flow rate of natural rubber. The higher value of the mooney viscosity means harder, less sticky, poor fluidity and low plasticity. On the contrary, the lower value of the mooney viscosity means softer, more sticky, better fluidity and higher plasticity.

The power meter 60 is coupled to the controller 10, the mooney sensor 50, and the rubber calender 30. When the mooney sensor 50 determines that the target mooney index 103 consistent with the actual mooney index, the power meter 60 records and obtains a power consumption value 61 from the rubber calender 30. In the first embodiment of the present disclosure, the power meter 60 subtracts the power recorded by the rubber calender 30 from the previous recorded power to obtain the power consumption value 61. That is to say, the power meter 60 may know the difference between different test procedures according to the continuous or discontinuous multiple test procedures.

The expansion ratio detection module 70 is coupled to the controller 10 and the rubber calender 30. The expansion ratio detection module 70 obtains an expansion ratio E=2D/G according to twice the thickness value D and the second roller pitch G. In other words, the expansion ratio detection module 70 may determine the difference in expansion ratio between different test procedures by the thickness value D measured and the second roller pitch G corresponding to the number of calendering the first rubber to be tested 201 used at the beginning (for example, the number of calendering the first rubber to be tested 201 is six times, the second roller pitch G is 0.065 mm). By comparing different rubber grades or different rubber types used in each test, rubber testers and rubber-related manufacturers may easily control material and cost by expansion ratio loss caused by processing factors such as calendering or heat treatment.

The rotation counter 80 is coupled to the controller 10, the temperature control module 40, the mooney sensor 50, and the rubber calender 30. When the temperature control module 40 determines that the first rubber to be tested 201 in the rubber calender 30 has reached the first temperature value 102, the rotation counter 80 counts the number of rotating 360 degrees of the two rollers 31 until the target mooney index being consistent with the actual mooney index, and the rotation counter 80 obtains a mechanical loss value 81 (shown as FIG. 7).

The specific gravity detection module 90 is coupled to the controller 10 and the rubber sampling module 20. The specific gravity detection module 90 applies a pressure of 2.3 metric tons to the third rubber to be tested 203, and then, the specific gravity detection module 90 obtains an actual specific gravity value S by detection a volume of the third rubber to be tested 203.

Figure 2:
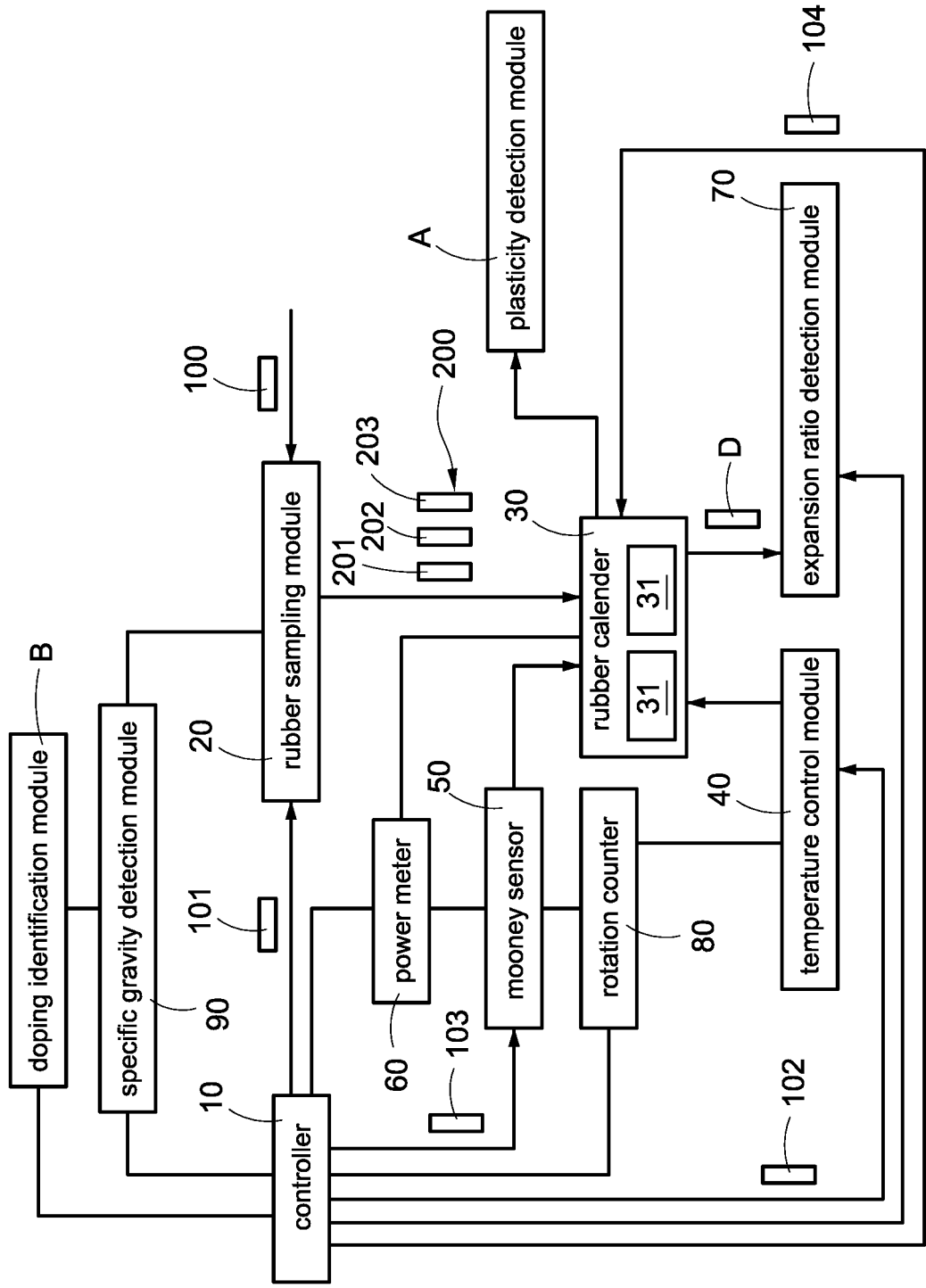
FIG. 2 is an architectural diagram of a second embodiment of a rubber detection system of the present disclosure.
Figure 3B:
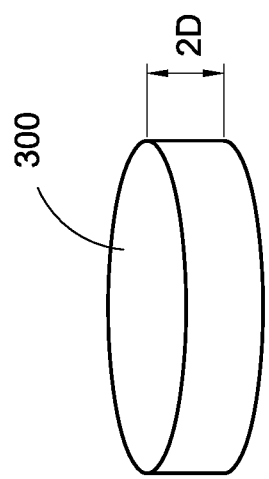
FIG. 3A, 3B are architectural diagrams of a cylinder is cut out by a plasticity detection module of the present disclosure.
Figure 3A:
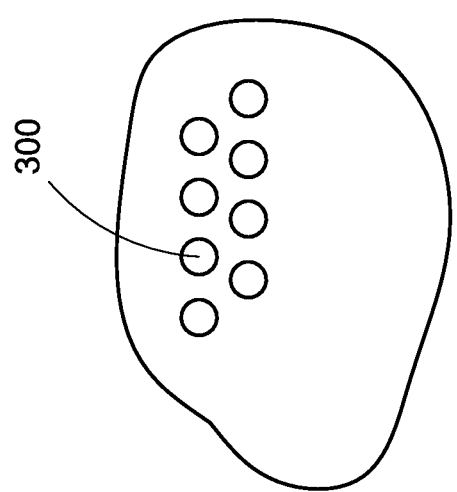
Figure 4:
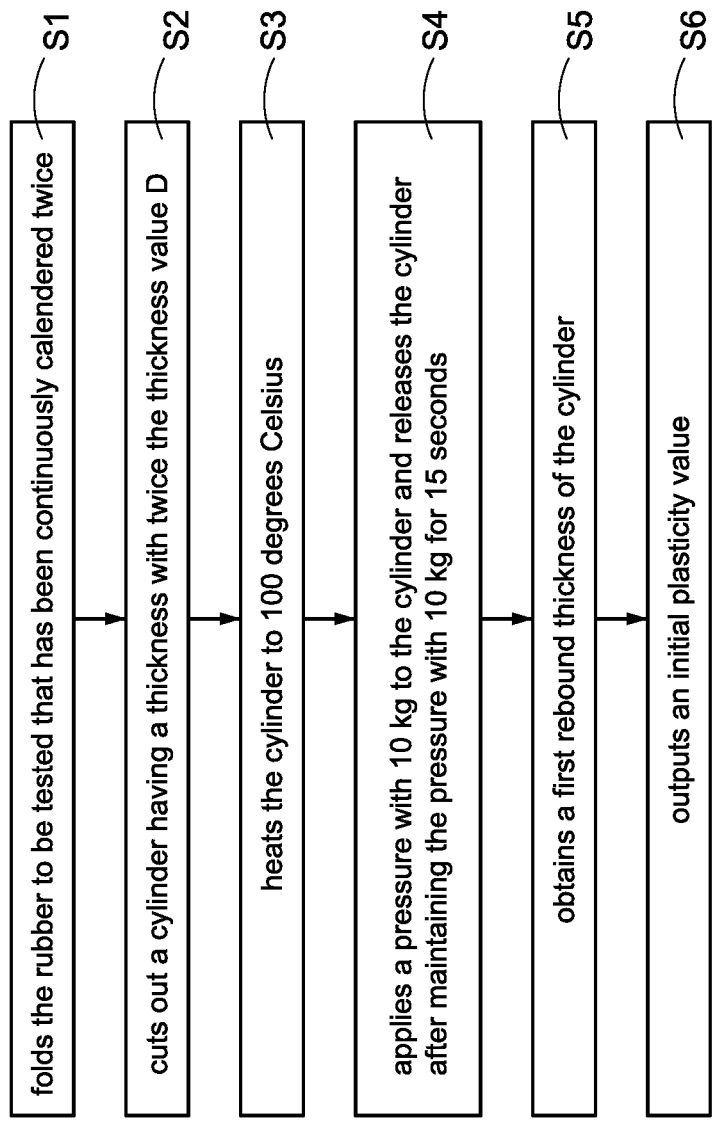
FIG. 4 is a flowchart showing outputting an initial plasticity value of the rubber detection system of the present disclosure.

Please refer to FIG. 2 to FIG. 4. FIG. 2 is an architectural diagram of a second embodiment of a rubber detection system of the present disclosure. FIG. 3A, 3B are architectural diagrams of a cylinder is cut out by a plasticity detection module of the present disclosure. FIG. 4 is a flowchart showing outputting an initial plasticity value of the rubber detection system of the present disclosure.

The second embodiment of the present disclosure is substantially the same as the first embodiment, but the second embodiment further includes a plasticity detection module A and a doping identification module B. The plasticity detection module A folds the second rubber to be tested 202 that has been continuously calendered two times (as shown in step S1 of FIG. 4), and cuts out a cylinder 300 (as shown in step S2 of FIG. 4) having a thickness with twice the thickness value D (that is 2D, as shown in FIG. 3A and FIG. 3B). Afterward, the plasticity detection module A heats the cylinder 300 to a second temperature value (as shown in step S3 of FIG. 4), and the plasticity detection module A applies a pressure with 10 kg to the cylinder 300 and releases the cylinder 300 after maintaining the pressure with 10 kg for 15 seconds (as shown in step S4 of FIG. 4). The second temperature value is 100 degrees Celsius. The plasticity detection module A obtains a first rebound thickness of the cylinder 300 after first impact and rebound moment for the cylinder 300 (as shown in step S5 of FIG. 4), and the plasticity detection module A outputs an initial plasticity value Po (as shown in step S6 of FIG. 4). The first rebound thickness has a minimum unit of 0.01 mm.

Figure 5:
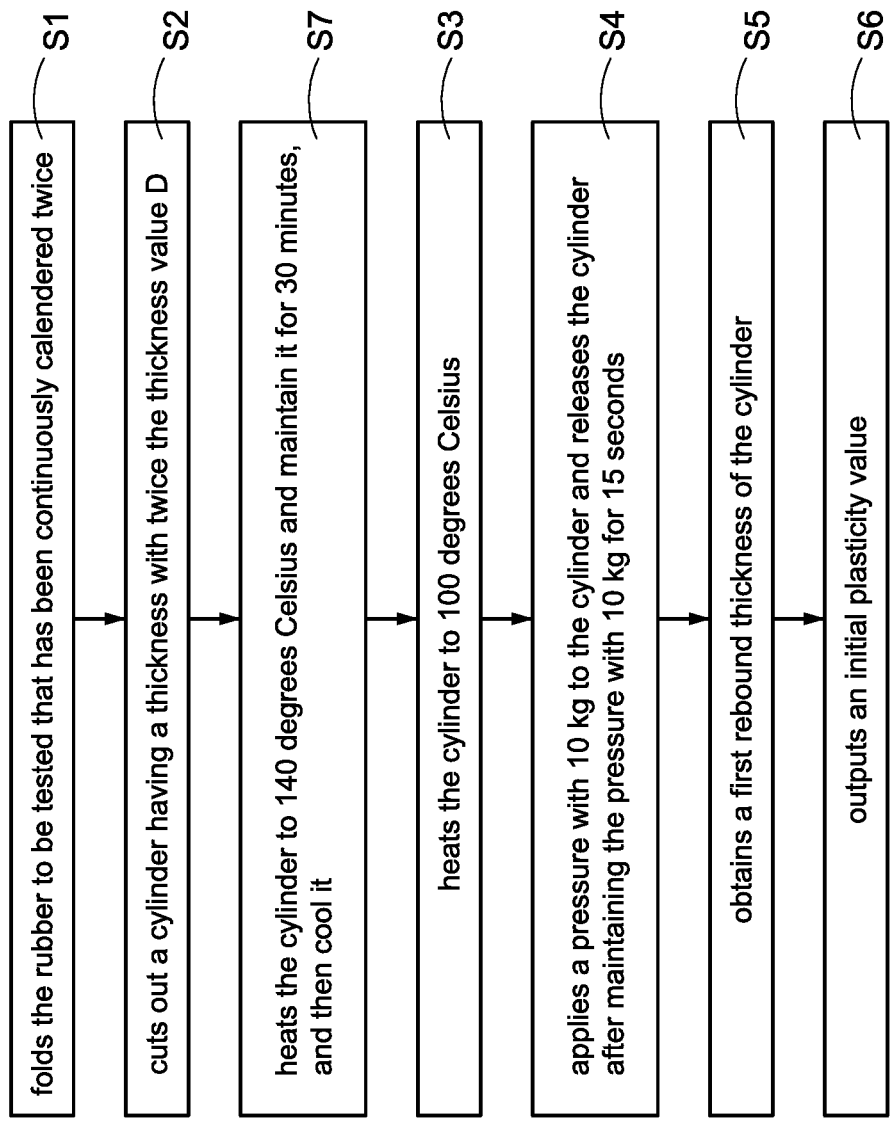
FIG. 5 is a flowchart showing outputting an aging plasticity value of the rubber detection system of the present disclosure.

FIG. 5 is a flowchart showing outputting an aging plasticity value of the rubber detection system of the present disclosure. It is based on the second embodiment of the present disclosure, and is substantially the same as the flow of outputting the initial plasticity value Po, but further includes a step S7 between the foregoing steps S2 and S3. The step S7 is to heat the cylinder 300 to 140 degrees Celsius and maintain the cylinder 300 for 30 minutes, and then, cool the cylinder 300 to perform heat aging treatment on the cylinder 300 to obtain an aging plasticity value $P_{30}$.

Further, a plasticity retention index (PRI) may be obtained by the initial plasticity value Po and the aging plasticity value $P_{30}$ obtained as described above:

$$PRI = \frac{P_{30}}{P_0} \times 100\%$$

The doping identification module B coupled to the controller 10 and the specific gravity detection module 90, and the doping identification module B obtains a doping ratio X of a skim rubber in the rubber raw material 100 according to the actual specific gravity value S and a target specific gravity value T. The skim rubber has a specific gravity value K and satisfies the following relationship:

$$X = \frac{(S - T)}{(K - T)} \times 100$$

The target specific gravity value T is 0.9149, and the specific gravity K of the skim rubber is 0.9783. When rubber slurry is concentrated by centrifugation, its by-product is condensed to form a rubber sheet. Because the smaller colloidal particles in the skim rubber have a larger surface adsorption area, they usually contain a high proportion of non-rubber materials such as natural protein (detected by nitrogen content $N_2$) and easily to increase sulfide that will cause rapid aging. Especially when the natural protein is mature, the skim rubber contains a high content of copper metal, which tends to cause the rubber to age and deteriorate in quality.

Figure 6:
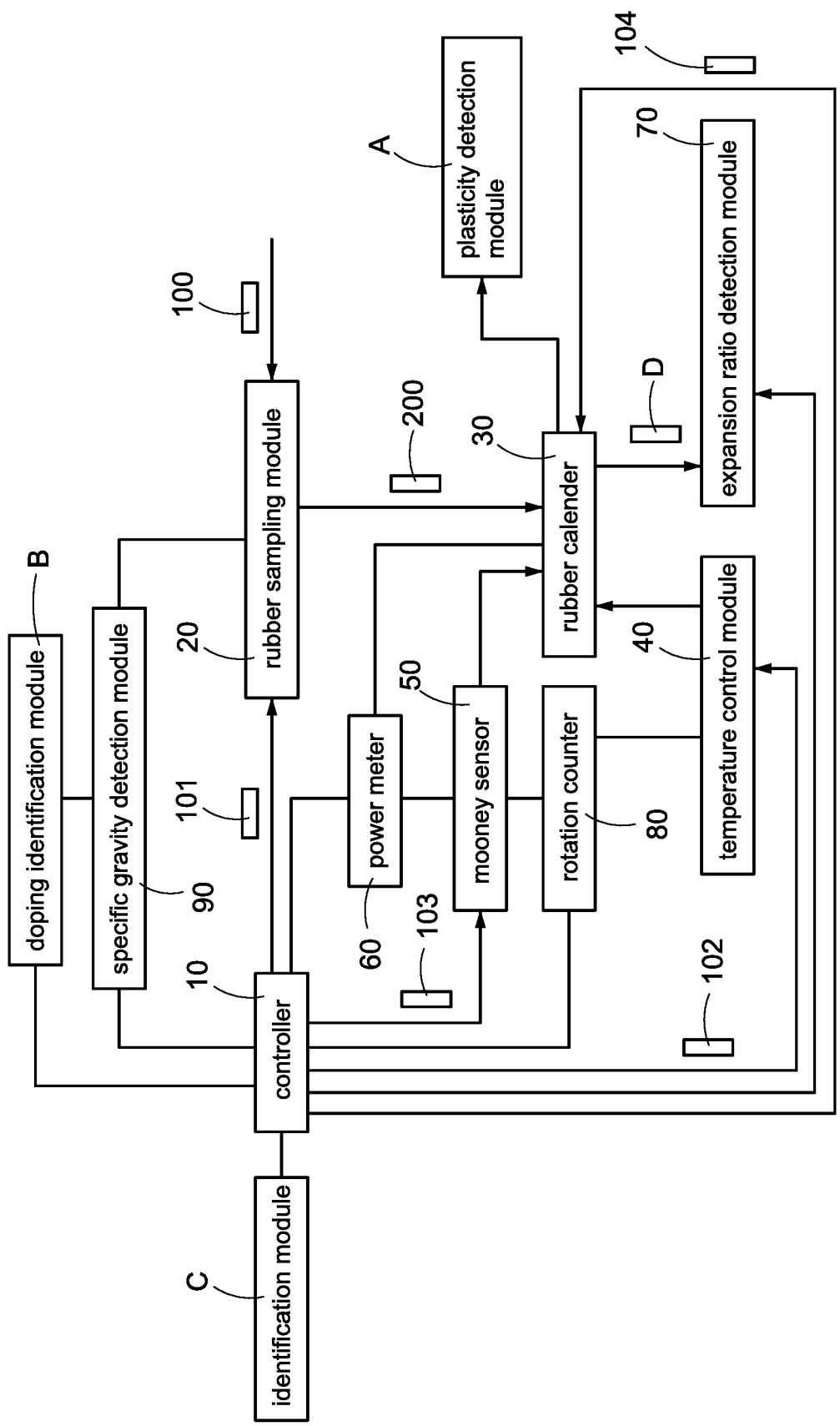
FIG. 6 is an architectural diagram of a third embodiment of a rubber detection system of the present disclosure.
Figure 7:
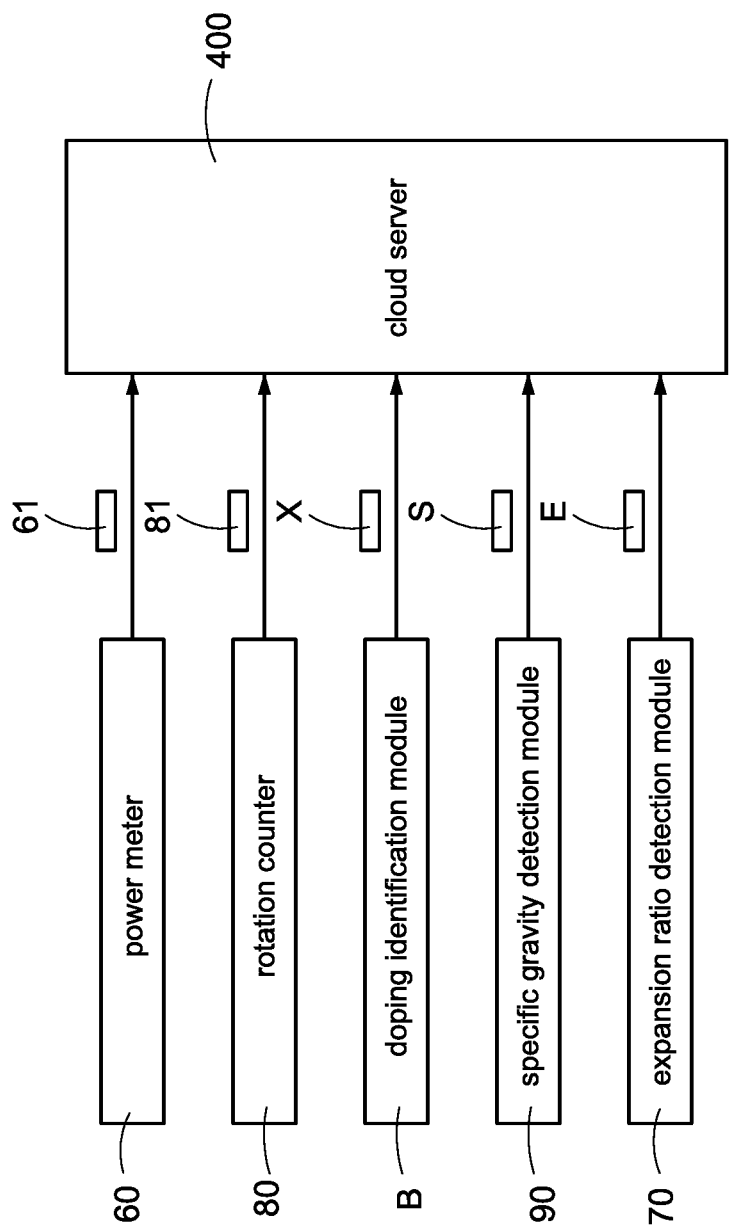
FIG. 7 is a schematic diagram of connection of stored data of a cloud server according to the present disclosure.

Please refer to FIG. 6 and FIG. 7. FIG. 6 is an architectural diagram of a third embodiment of a rubber detection system of the present disclosure. FIG. 7 is a schematic diagram of connection of stored data of a cloud server according to the present disclosure.

The third embodiment of the present disclosure is substantially the same as the second embodiment, but the third embodiment further includes an identification module C and a cloud server 400. The identification module C coupled to the controller 10, and the identification module C controls an access authority of the power consumption value 61, the expansion ratio E, the mechanical loss value 81, the actual specific gravity value S and the doping ratio X by combination with at least one of NFC, RFID, fingerprint, voiceprint, face recognition, retina, and password. The cloud server 400 stores the power consumption value 61, the expansion ratio E, the mechanical loss value 81, the actual specific gravity value S, and the doping ratio X.

When operating the rubber detection system, the controller 10 causes the rubber sampling module 20 to obtain the first rubber to be tested 201 according to the first weight value, the controller 10 causes the rubber sampling module 20 to obtain the second rubber to be tested 202 according to the second weight value, and the controller 10 causes the rubber sampling module 20 to obtain the third rubber to be tested 203 according to the third weight value.

Afterward, the temperature control module 40 maintaining the first rubber to be tested 201 or the second rubber to be tested 202 to have the first temperature value 102. When the temperature control module 40 determines that the first rubber to be tested 201 in the rubber calender 30 has reached the first temperature value 102, the two rollers 31 spaced apart from each other by the first roller pitch and continuously calendering the first rubber to be tested 201 at least six times. When the temperature control module 40 determines that the second rubber to be tested 202 in the rubber calender 30 has reached the first temperature value 102, the two rollers 31 spaced apart from each other by the second roller pitch G and continuously calendering the second rubber to be tested 202 two times, and the rubber calender 30 outputs the second rubber to be tested 202 having a thickness value D.

Finally, the expansion ratio detection module 70 obtains the expansion ratio $E=2D/G$ according to twice the thickness value D and the second roller pitch G. The rotation counter 80 and the power meter 60 respectively obtain the mechanical loss value 81 and the power consumption value 61 through the actual mooney index obtained by the mooney sensor 50 and the target mooney index generated by the controller 10. The specific gravity detection module 90 may obtain the actual specific gravity value S by sorting or synchronizing with the foregoing steps.

To this end, according to the rubber has a specific number of calendering the rubber and the rubber to be tested has weight value as a specific sampling weight, the present disclosure can accurately control the second roller pitch G of the rubber calender 30 (the second roller pitch G is changed in a minimum unit of 0.001 mm depending on the number of calendering the rubber) and temperature value of the rubber to be tested (as the first temperature value 102 or the second temperature value). Thereby obtaining the accurate the expansion ratio E, the power consumption value 61, the mechanical loss value 81, the actual specific gravity value S, and the doping ratio X, and achieving the purpose to reduce the production cost of the rubber-related manufacturing industry.

When the number of calendering the second rubber to be tested 202 is six times, the second roller pitch G is 0.065 mm. When the number of calendering the second rubber to be tested 202 is ten times, the second roller pitch G is 0.075 mm. When the number of calendering the second rubber to be tested 202 is sixteen times, the second roller pitch G is 0.085 mm. When the number of calendering the second rubber to be tested 202 is twenty-two times, the second roller pitch G is 0.095 mm. When the number of calendering the second rubber to be tested 202 is twenty-eight times, the second roller pitch G is 0.125 mm. When the number of calendering the second rubber to be tested 202 is thirty-four times, the second roller pitch G is 0.145 mm. However, the present disclosure is not limited thereto.

The rubber industry knows that the closer to the equator, the higher the average natural rubber production capacity, the better the average quality and the thicker the secreted gum. The above-mentioned technology has accumulated many years of experience and research and development design, and can be a calculation model and testing equipment for natural rubber, which can test and calculate the loss of specific gravity, loss of rubber expansion rate, loss of power consumption, manpower and machine wear. It is possible to calculate the misunderstanding of the price and value of the natural rubber of various grades and numbers, and can analyze the comparative data of the price and value of the natural rubber. From then on, it can be avoided to the greatest extent that the label of the natural rubber is incorrect, or because the lack of correct data, the procurement personnel only purchase according to their rules of thumb or market conditions, or human error, resulting in invisible losses. Especially for companies with a large amount of natural rubber, the use of the aforementioned technology will certainly reduce the cost of raw material procurement, or increase the production cost due to non-optimal specifications, and also avoid the mistakes of the procurement staff or the opaque zone. It saves a lot of money and avoids the waste of global resources for the human, tire and natural rubber industries.

The above is only a detailed description and drawings of the preferred embodiments of the present disclosure, but the features of the present disclosure are not limited thereto, and are not intended to limit the present disclosure. All the scope of the present disclosure shall be subject to the scope of the following claims. The embodiments of the spirit of the present disclosure and its similar variations are intended to be included in the scope of the present disclosure. Any variation or modification that can be easily conceived by those skilled in the art in the field of the present disclosure can be covered by the following claims.

What is claimed is:

1. A rubber detection system for rubber raw material, comprising: a controller configured to produce a first weight value, a second weight value, a third weight value, a first temperature value, a target mooney index, a first roller pitch and a second roller pitch, a rubber sampling module coupled to the controller, and the rubber sampling module configured to obtain a first rubber to be tested consistent with the first weight value, and the rubber sampling module configured to sample the rubber raw material according to the second weight value to obtain a second rubber to be tested consistent with the second weight value, and the rubber sampling module configured to sample the rubber raw material according to the third weight value to obtain a third rubber to be tested consistent with the third weight value, a rubber calender coupled to the controller and the rubber sampling module, the rubber calender including two rollers arranged in parallel, a temperature control module coupled to the controller and the rubber calender, the temperature control module configured to maintain the first rubber to be tested to be tested to have the first temperature value, a mooney sensor coupled to the controller, the temperature control module, and the rubber calender, a power meter coupled to the controller, the mooney sensor, and the rubber calender, wherein the mooney sensor is configured to determine if the target mooney index is consistent with the actual mooney index and the power meter is configured to record and obtain a power consumption value from the rubber calender when the mooney sensor determines that the target mooney index is consistent with the actual mooney index, an expansion ratio detection module coupled to the controller and the rubber calender, a rotation counter coupled to the controller, the temperature control module, the mooney sensor, and the rubber calender, and a specific gravity detection module coupled to the controller and the rubber sampling module, the rubber detections system further comprising a plasticity detection module, the plasticity detection module configured to fold the second rubber to be tested that has been continuously calendered two times, and the plasticity detection module configured to cut out a, and then the plasticity detection module configured to heat the cylinder to a second temperature value, and configured to apply a pressure with 10 kg to the cylinder and release the cylinder after maintaining the pressure with 10 kg for 15 seconds, the plasticity detection module configured to obtain a first rebound thickness of the cylinder after a first impact and a rebound moment for the cylinder, wherein the first rebound thickness has a minimum unit of 0.01 mm.

2. The rubber detection system in claim 1, wherein the first weight value is 360 grams, the second weight value is 25 grams, and the third weight value is 1 kilogram.

3. The rubber detection system in claim 1, wherein the first temperature value is 25 degrees Celsius.

4. The rubber detection system in claim 1, wherein the target mooney index has a mooney viscosity between 61.07 and 91.06.

5. The rubber detection system in claim 1, wherein the first roller pitch is 1.65 mm, and the second roller pitch is 0.065 mm.

6. The rubber detection system in claim 1, wherein the two rollers include a front roller and a rear roller.

7. The rubber detection system in claim 6, wherein when the two rollers are configured to continuously calender the first rubber to be tested, the speed ratio of the two rollers is 1:1.4.

8. The rubber detection system in claim 1, wherein the power meter is configured to obtain the power consumption value by subtracting a power of a previous record from a power of a current record of the rubber calender.

9. The rubber detection system in claim 1, wherein the temperature control module is a water-cooled chiller.

10. The rubber detection system in claim 1, wherein the second temperature value is 100 degrees Celsius.

11. The rubber detection system in claim 1, further comprising a doping identification module coupled to the controller and the specific gravity detection module, and the doping identification module configured to obtain a doping ratio X of a skim rubber in the rubber raw material according to the actual specific gravity value S and a target specific gravity value T, wherein the skim rubber has a specific gravity value K and satisfies the following relationship: $X=((S-T))/((K-T))\times 100$.

12. The rubber detection system in claim 11, wherein the target specific gravity value T is 0.9149, and the specific gravity value K of the skim rubber is 0.9783.

13. The rubber detection system of claim 11, further comprising an identification module, the identification module coupled to the controller, and the identification module configured to control an access authority of the power consumption value, the expansion ratio E, the mechanical loss value, the actual specific gravity value S and the doping ratio X by combination with at least one of Near Field Communication (NFC), Radio-frequency identification (RFID), fingerprint, voiceprint, face recognition, retina, and password.

14. The rubber detection system in claim 13, further comprising a cloud server, the cloud server configured to store the power consumption value, the expansion ratio E, the mechanical loss value, the actual specific gravity value S, and the doping ratio X.

15. The rubber detection system in claim 1, further comprising a plasticity detection module, the plasticity detection module configured to fold the second rubber to be tested that has been continuously calendered two times, and configured to cut out a cylinder, and then, the cylinder being heated to 140 degrees Celsius and being cooled after the cylinder being maintained 140 degrees Celsius for 30 minutes, finally, the plasticity detection module configured to heat the cylinder to a second temperature value, and the plasticity detection module configured to apply a pressure with 10 kg to the cylinder and release the cylinder after maintaining the pressure with 10 kg for 15 seconds, the plasticity detection module configured to obtain a first rebound thickness of the cylinder after a first impact and a rebound moment for the cylinder, wherein the first rebound thickness has a minimum unit of 0.01 mm.

16. The rubber detection system in claim 15, wherein the second temperature value is 100 degrees Celsius.

* * * * *